(12) United States Patent
Ha et al.

(10) Patent No.: US 10,276,310 B2
(45) Date of Patent: Apr. 30, 2019

(54) CARBON FIBER ELECTRODE, WIRE-TYPE SUPERCAPACITOR INCLUDING THE CARBON FIBER ELECTRODE AND $NO_2$ SENSOR AND UV SENSOR INCLUDING THE SUPERCAPACITOR

(71) Applicant: Korea University Research and Business Foundation, Seoul (KR)

(72) Inventors: Jeong Sook Ha, Seoul (KR); Kayeon Keum, Seoul (KR); Daeil Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/663,998

(22) Filed: Jul. 31, 2017

(65) Prior Publication Data
US 2018/0061586 A1 Mar. 1, 2018

(30) Foreign Application Priority Data
Jul. 29, 2016 (KR) .................. 10-2016-0097408

(51) Int. Cl.
*H01G 11/24* (2013.01)
*G01J 1/42* (2006.01)
(Continued)

(52) U.S. Cl.
CPC .............. *H01G 11/24* (2013.01); *G01J 1/429* (2013.01); *G01N 27/4075* (2013.01);
(Continued)

(58) Field of Classification Search
CPC ........ H01G 11/06; H01G 11/26; H01G 11/32; H01G 11/34; H01G 11/40; H01G 11/46; H01G 11/50; H01G 11/86; H01G 11/24
See application file for complete search history.

(56) References Cited

U.S. PATENT DOCUMENTS

| | | | |
|---|---|---|---|
| 5,336,254 A * | 8/1994 | Brennen | A61N 1/0587 607/129 |
| 2009/0225498 A1* | 9/2009 | Lee | H01G 11/46 361/523 |

(Continued)

FOREIGN PATENT DOCUMENTS

KR 20150092923 A 8/2015

OTHER PUBLICATIONS

Xie et al., "Stabilizing an amorphouse V2O5/carbon nanotube paper electrode with conformal TiO2 coating by atomic layer deposition for lithium ion batteries," J. Mater. Chem. A (20016); 4:537-544.

*Primary Examiner* — Nguyen T Ha
(74) *Attorney, Agent, or Firm* — Fox Rothschild LLP

(57) ABSTRACT

A wire shaped carbon fiber electrode is disclosed. The carbon fiber electrode includes braided strings of carbon fiber. The carbon fiber electrode is fabricated in a simple process, facilitating its practical application to clothes. In addition, the carbon fiber electrode possesses high capacitance and structural stability and is easily applicable to various wearable devices. Also disclosed are a wire-type supercapacitor including the carbon fiber electrode, a $NO_2$ sensor including the supercapacitor, and a UV sensor including the supercapacitor.

9 Claims, 12 Drawing Sheets

(51) Int. Cl.
*G01N 27/407* (2006.01)
*H01G 11/40* (2013.01)
*H01G 11/26* (2013.01)
*H01G 11/36* (2013.01)
*H01G 11/52* (2013.01)
*H01G 11/56* (2013.01)
*H01G 11/46* (2013.01)

(52) U.S. Cl.
CPC ............. *H01G 11/26* (2013.01); *H01G 11/40* (2013.01); *H01G 11/36* (2013.01); *H01G 11/46* (2013.01); *H01G 11/52* (2013.01); *H01G 11/56* (2013.01); *Y02E 60/13* (2013.01)

(56) References Cited

U.S. PATENT DOCUMENTS

| | | | | |
|---|---|---|---|---|
| 2011/0058309 | A1* | 3/2011 | Eguchi | H01M 4/0404 361/503 |
| 2011/0170236 | A1* | 7/2011 | Young | H01G 9/016 361/502 |
| 2012/0219844 | A1* | 8/2012 | Tsutsumi | H01G 11/06 429/153 |
| 2013/0217289 | A1* | 8/2013 | Nayfeh | H01G 11/30 442/301 |
| 2016/0058316 | A1* | 3/2016 | Vitale | A61B 5/0478 600/309 |
| 2016/0190859 | A1* | 6/2016 | Blum | H02J 7/025 348/372 |
| 2017/0309409 | A1* | 10/2017 | Kim | H01G 11/36 |

* cited by examiner

Figs. 12a and 12b
(a)
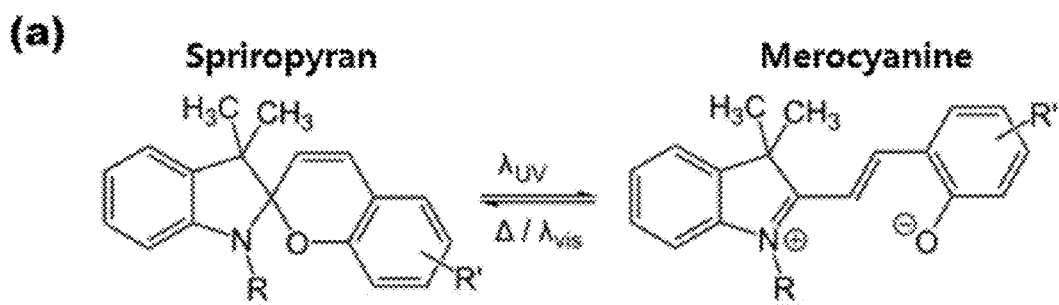
(b)
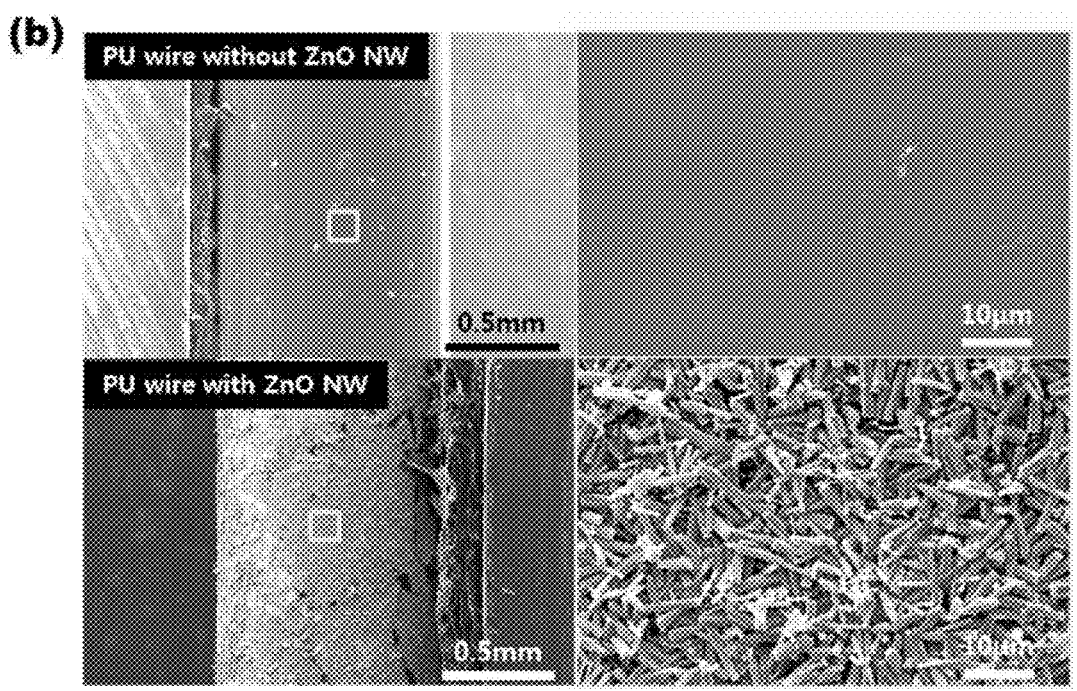
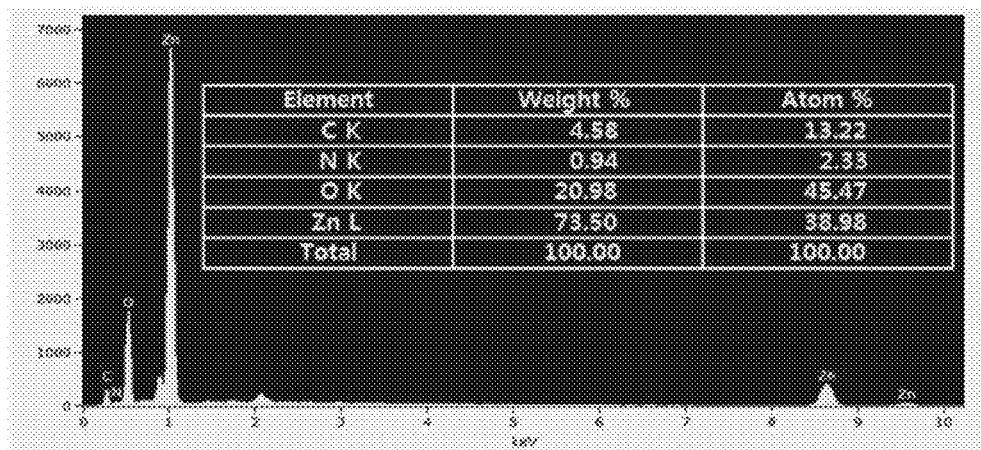

CARBON FIBER ELECTRODE, WIRE-TYPE SUPERCAPACITOR INCLUDING THE CARBON FIBER ELECTRODE AND NO₂ SENSOR AND UV SENSOR INCLUDING THE SUPERCAPACITOR

BACKGROUND OF THE INVENTION

1. Field of the Invention

The present invention relates to a carbon fiber electrode, a wire-type supercapacitor including the carbon fiber electrode, a nitrogen dioxide ($NO_2$) sensor including the supercapacitor, and an ultraviolet (UV) sensor including the supercapacitor.

2. Description of the Related Art

Personal electronics are advancing toward an era when the pursuit of multifunctionality and convenience. This advancement requires not only miniaturization of the size of devices but also incorporating them into wearable materials (e.g., cloth fabrics and accessories) for their ease of use. Integration of lightweight, highly deformation-resistant devices into one wearable smart power system is also one of the critical research fields. The realization of such systems requires various forms of stretchable and flexible energy storage devices with high capacitance.

Planar supercapacitors reported hitherto suffer from difficulty in directly integrating them onto fabrics due to their 2-dimensional structure and are unsuitable for use in wearable systems because of their structural and textural differences from fabric fibers when attached or adhered to cloth. In order to solve these problems, there is a need to change the inherent structure of supercapacitors.

In recent years, wire-type supercapacitors for the construction of wearable systems have been actively investigated. One-dimensional (1D) wire-type supercapacitors can be directly integrated into cloth and can also be integrated with fabric during manufacture of the fabric, facilitating the fabrication of the devices. Wire-type supercapacitors can be fabricated in various shapes due to their flexibility. Based on these advantages, extensive research on wire-type supercapacitors is actively underway and show that wire-type supercapacitors are suitable energy storage devices for wearable systems, for example, they can be applied as power sources for turning light-emitting diodes (LEDs) on.

In this connection, wearable devices including integrated flexible yarn supercapacitors with reduced graphene oxide (rGO)/Ni-coated polyester electrodes and fabric nanogenerators was reported in X. Pu, L. Li, M. Liu, C. Jiang, C. Du, Z. Zhao, W. Hu and Z. L. Wang, Adv. Mater., 2016, 28, 98. The wearable devices are used to activate light emitting diodes (LEDs) of fabrics. Further, flexible yarn supercapacitors with rGO/Ni-coated cotton fiber electrodes as power sources for LEDs were reported in L. Liu, Y Yu, C Yan, K. Li and Z. Zhen, Nat. Commun., 2015, 6, 7260. The supercapacitors are knitted into various fabric patterns using an embroidery machine. Furthermore, research on carbon fiber-based hybrid fiber type supercapacitors having a high potential window was reported in S. T. Senthilkumar, J. Kim, Y. Wang, H. Huang and Y. Kim, J. Mater. Chem. A, 2016, 4, 4934. The supercapacitors are used to improve the performance of wire-type supercapacitors with asymmetric electrodes. However, the application of the supercapacitors is limited only to the activation of LEDs.

Most previously reported wire-type supercapacitors employ solid-state water-based electrolytes, which also act as separators. However, such electrolytes have low energy density owing to their low voltage range. Thus, there exists a need to increase the energy density of electrolytes by extending their voltage range to improve the performance of supercapacitors.

Specifically, the use of a supercapacitor as an energy storage device requires an increased energy density (E) of the supercapacitor. The energy density (E) can be calculated by $E=0.5CV^2$. This equation shows that capacitance (C) and voltage (V) need to be improved when it is desired to increase the energy density. The capacitance is determined by the kind of an electrode material and the interaction between the electrode material and an electrolyte. In most wire-type supercapacitors that are currently in use, pseudo-capacitive materials capable of enhancing the capacitance through redox reactions are added to carbon-based materials forming electric double layers.

The voltage range of an electrolyte is determined mainly by a solvent used in the electrolyte. Although easy-to-handle, environmentally safe water-based electrolytes are widely used, an improvement in the energy density of the electrolytes is limited by their low voltage range (<1V). In numerous attempts to overcome this limitation, electrolytes based on organic materials are introduced or asymmetric supercapacitors using different electrodes as the cathode and anode are introduced. Many electrolytes with improved voltage range have been developed, for example, ionic liquids that exist as liquid-state salts at room temperature. Ionic liquids have good thermal and chemical stability, low melting point, reduced risk of fire, and high ionic conductivity. [EMIM][TFSI] is an ionic liquid that has a low melting point (−17 □), a high conductivity (8.8 mS/cm), and a high voltage range (4.1 V), showing its applicability as an electrolyte solvent.

Wire-type supercapacitors developed hitherto have not yet been put into practical use in wearable systems because of their limited application scope. Thus, the introduction of more diverse and life-related applications is necessary for the realization of practical wearable systems. Existing sensors require complicated fabrication processes and most of them are fabricated into 2-dimensional structures, such as planar structures, making it difficult to directly integrate them into cloth. Thus, there exists a need for wire-type supercapacitors for practical use in wearable systems that are easy to integrate into cloth and can be fabricated in a convenient manner.

SUMMARY OF THE INVENTION

The present invention has been made in view of the problems of the prior art and is intended to provide a carbon fiber electrode that is fabricated in a simple process, facilitating its practical application to clothes, possesses high capacitance and structural stability, and is easily applicable to various wearable devices, a wire-type supercapacitor including the carbon fiber electrode, a $NO_2$ sensor including the supercapacitor, and a UV sensor including the supercapacitor.

One aspect of the present invention provides a wire shaped carbon fiber electrode including braided strings of carbon fiber.

According to one embodiment of the present invention, the carbon fiber electrode may include three strings of carbon fiber.

According to a further embodiment of the present invention, the carbon fiber electrode may be surface coated with carbon nanotubes.

According to another embodiment of the present invention, the carbon nanotubes may be surface coated with $V_2O_5$ nanowires.

A further aspect of the present invention provides a wire-type supercapacitor including the carbon fiber electrode, a solid-state electrolyte, and a separator.

According to one embodiment of the present invention, the solid-state electrolyte may include 1-ethyl-3-methylimidazolium bis(trifluoromethylsulfonyl)imide, LiCl, and $Al_2O_3$ nanoparticles.

According to a further embodiment of the present invention, the separator may be a cellulose separator.

Another aspect of the present invention provides a $NO_2$ sensor including the supercapacitor.

Yet another aspect of the present invention provides a UV sensor including the supercapacitor.

The carbon fiber electrode of the present invention is fabricated in a simple process, facilitating its practical application to clothes. In addition, the carbon fiber electrode of the present invention possesses high capacitance and structural stability and is easily applicable to various wearable devices. The wire-type supercapacitor, the $NO_2$ sensor, and the UV sensor of the present invention utilize the advantages of the carbon fiber electrode.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 12a and 12b show (a) molecular models of a photoreaction between SP and MC and (b) SEM images taken from PU wires before (top) and after (bottom) the growth of ZnO NWs.

DETAILED DESCRIPTION OF THE INVENTION

Figure 1A:
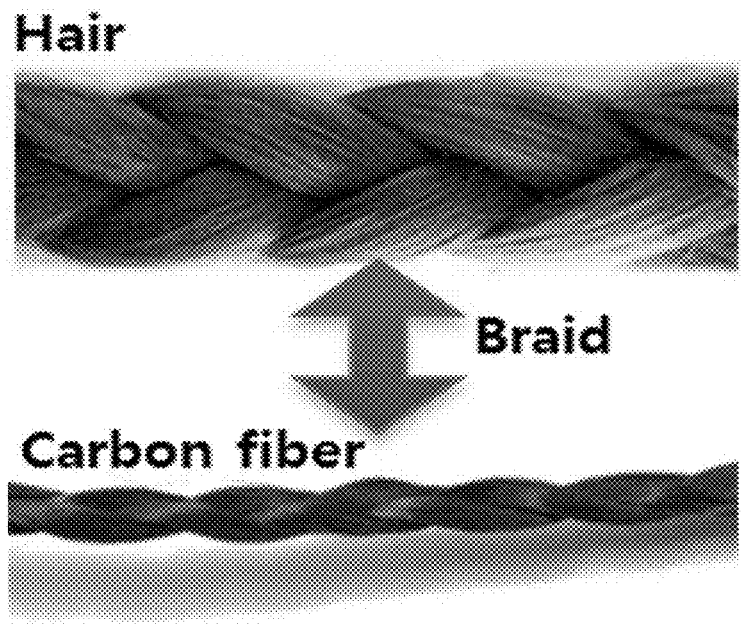
FIG. 1a is an optical image of a braided carbon fiber comprised of three pieces of carbon fiber.

The present invention will now be described in more detail.

In the present invention, a carbon fiber-based electrode applicable to various wearable devices is fabricated, a wire-type supercapacitor using the carbon fiber-based electrode is fabricated, and the supercapacitor is applied to practical sensors. The capacitance of the carbon fiber-based electrode can be improved by sequential coating of carbon nanotubes and $V_2O_5$ nanowires on the surface of the electrode. The supercapacitor uses an ionic liquid-based electrolyte including a lithium salt to ensure improved capacitance and optimum viscosity.

Specifically, the present invention provides a wire shaped carbon fiber electrode including braided strings of carbon fiber. The carbon fiber electrode may include three strings of carbon fiber. For example, the use of three strings of carbon fiber allows the carbon fiber electrode to retain its wire shape and facilitates control over the length and thickness of the carbon fiber-based electrode compared to the use of only two strings of carbon fiber.

As described above, the capacitance of the electrode can be improved by sequential coating of carbon nanotubes and $V_2O_5$ nanowires on the surface of the electrode.

The present invention also provides a wire-type supercapacitor including the carbon fiber electrode, a solid-state electrolyte, and a separator. The solid-state electrolyte is based on an ionic liquid including a lithium salt and may include 1-ethyl-3-methylimidazolium bis(trifluoromethylsulfonyl)imide, LiCl, and $Al_2O_3$ nanoparticles.

The separator may be a cellulose separator. The separator may have an average pore diameter of about 7 μm. The separator exhibits good wettability on the electrolyte and can effectively insulate electrodes.

The present invention also provides a $NO_2$ sensor and a UV sensor, each of which uses the wire-type supercapacitor. The $NO_2$ sensor can stably detect $NO_2$ gas on fabric for a long time. The UV sensor can be attached to fabric to detect UV in color or quantitatively photocurrent.

The present invention will be explained in more detail with reference to the following examples. These examples are provided to assist in understanding the invention and are not intended to limit the scope of the invention.

Experimental Section

Fabrication of Carbon Fiber/Carbon Nanotubes/$V_2O_5$ NW Electrode

Three strings of carbon fiber (Kenis, Japan) were braided to form a wire shaped electrode. The braided carbon fiber electrode was then dipped into a carbon nanotube-COOH aqueous solution (1 mg/mL) for 3 s and then dried at 65° C. This was repeated six times to thoroughly coat the carbon fiber surface with carbon nanotube-COOH. The carbon nanotube-coated braided carbon fiber electrode was dipped again in an aqueous solution of sol-gel grown $V_2O_5$ nanowires (1 mg/mL) for 1 min and then dried at 65° C. This was repeated three times to thoroughly coat $V_2O_5$ nanowires onto the carbon nanotube-coated braided carbon fiber surface.

Synthesis of Solid-State Electrolyte

A Li salt-containing solid-state electrolyte was synthesized using [EMIM][TFSI] (Sigma Aldrich), LiCl (Sigma Aldrich) and $Al_2O_3$ nanoparticles (10 nm, Sigma Aldrich). First, 1 g of LiCl and 10 mL of [EMIM][TFSI] were mixed in a mortar for 10 min. After 1 g of $Al_2O_3$ nanoparticles was added to the slurry for viscosity control, the slurry was mixed for 10 min. Lastly, 10 mL of [EMIM][TFSI] and 1 g of $Al_2O_3$ nanoparticles were added once more to the slurry which was then mixed for 20 min.

Fabrication of Wire Shaped Supercapacitor

Wire shaped supercapacitors were fabricated using electrodes fabricated above, the synthesized solid-state electrolyte and a cellulose separator (KIMTECH SCIECE Wiperes Medium, Yuhan-Kimberly Professional). Specifically, a 10 cm-long copper wire was wrapped around each electrode to function as a current collector. These electrodes were rolled up with a cellulose separator with an area of 3 cm×6 cm. Next, the electrodes with cellulose separator were uniformly painted with the synthesized solid-state electrolyte using a brush. The electrolyte-coated electrodes were then inserted in thermally shrinkable tubes (7 cm in diameter) and the whole assembly was heat-treated at 100° C. Finally, both ends of the fabricated wire-type supercapacitor were sealed with epoxy (Devcon, USA).

Fabrication of Wire Shaped $NO_2$ Gas and UV Sensors

A $NO_2$ gas sensor was fabricated by dipping a wool wire in carbon nanotube solution (1 mg/mL) until a resistance of $\sim 10^8 \Omega$ was measured at 1 V. Two different wire-type UV sensors were fabricated. The first UV sensor was fabricated by coating fabricated by coating a spiropyran solution (dispersed in ethanol, Sigma Aldrich) onto a polyurethane fiber. The color of the spiropyran solution changes in response to UV and the color change is visible to the naked eye. The second UV sensor was fabricated by growing ZnO nanowires on a polyurethane fiber. The second UV sensor can measure photocurrent. Polyurethane fibers were immersed into an aqueous solution of zinc acetate dehydrate [$Zn(CH_3COO)_2.2H_2O$] (0.01 M). Then, 2 mL of a potassium hydroxide aqueous solution (KOH, 0.03 M) was added to the aforementioned solution, which was ultra-sonicated for 15 min. After the reaction at 65° C. for 15 min, the polyurethane fibers were removed from the solution and dried at 50° C. for no more than 5 min. The soak-coating process of ZnO seed layer was then repeated. The polyurethane wires formed with seed layer were added to an equimolar aqueous solution (0.05 M) of hexamethylenetetramine and zinc nitrate hexahydrate [$Zn(NO_3)_2.6H_2O$] and ZnO nanowires were allowed to grow at 95° C. for 20 h. Finally, the ZnO nanowire-grown polyurethane fibers were dried at 60° C. to remove residual water.

Characterization

Sample images were acquired using an EOS 7D (Canon) camera and field-emission scanning electron microscopy (FESEM) was carried out with an energy-dispersive X-ray (EDX) setup (S-4800, Hitachi). The electrochemical performance of wire-type supercapacitors was analyzed by cyclic voltammetry (CV), galvanostatic charge/discharge, and Nyquist plots using an electrochemical analyzer (Compact Stat, Ivium Technologies). The rheological properties of solid-state electrolytes were measured using an MCR rheometer (MCR 301, Anton Paar). The pore distribution of separators was analyzed by using the image analysis program (ImageJ, NIH). UV and $NO_2$ gas detection characteristics were measured with a probe station system (4155C, MS-TECH and Agilent) under 365 nm UV irradiation and 200 ppm $NO_2$ gas exposure, respectively.

Results and Discussion

Figure 2:
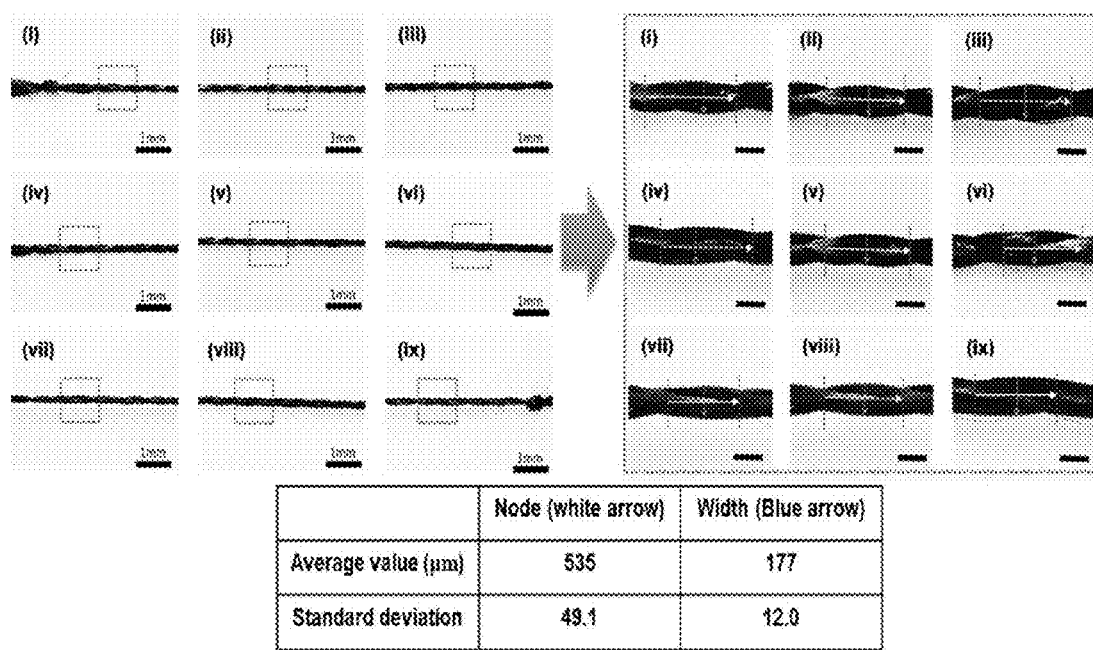
FIG. 2 shows optical images showing the distributions of length and thickness measured for a single braided carbon fiber measured at various positions.

FIG. 1a shows an optical image of a braided carbon fiber comprised of three pieces of carbon fiber, similar in appearance to braided hair. Whereas two-piece braided carbon fiber suffered from difficulty in retaining its wire shape, the three-piece braided carbon fiber retained its wire shape, making it much easier to produce wire-type supercapacitors with controlled length and thickness. FIG. 2 shows optical images showing the distribution of length and thickness for a single braided carbon fiber measured at various positions.

Figure 1B:
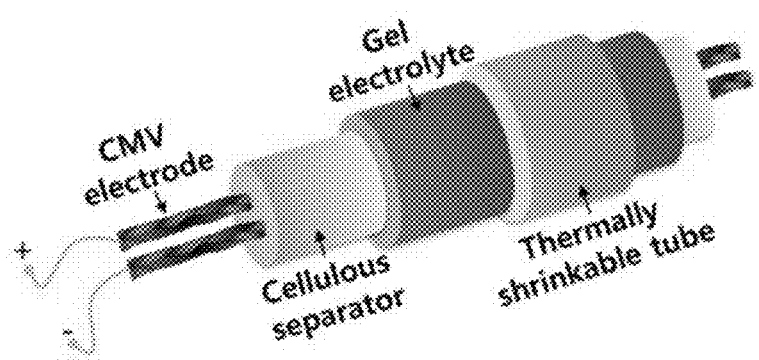
FIG. 1b is a schematic diagram showing a wire-type supercapacitor of the present invention.

The braided carbon fiber has an average node length and thickness of 535 and 177 μm, respectively. FIG. 1b shows a schematic of the fabricated wire-type supercapacitor, featuring CF/MWNT/$V_2O_5$ NWs (CMV) as electrodes, cellulose paper as a separator, Li ion-containing ionic liquid as a solid-state electrolyte, and thermally shrinkable tubes for encapsulation to ensure the water-proofing and insulating property. Referring to FIG. 1b, the wire-type supercapacitor can be deformed into various shapes, such as knotted and folded structures.

In the present invention, one-dimensional $V_2O_5$ nanowires synthesized via sol-gel method were used as electrode materials with multi-walled nanotubes (MWNTs) since 1D nanostructures have been considered to enhance the electrochemical performance by providing short diffusion paths for electrons and ions, fast redox reactions, and large surface area. Also, to improve the performance of WSCs, it is important to utilize cost-effective materials which can enhance energy storage capability.

Figure 1C:
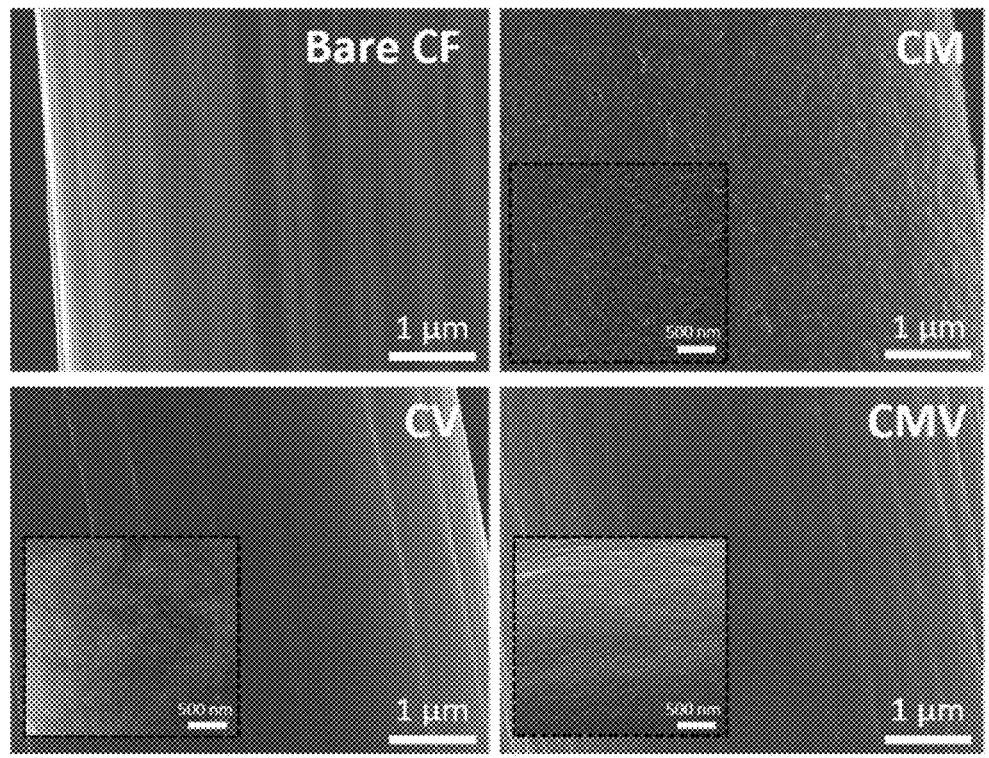
FIG. 1c shows SEM images of a bare carbon fiber (CF) electrode, a carbon fiber electrode coated with MWNTs (CM), a carbon fiber electrode coated with $V_2O_5$ NWs (CV), and a carbon fiber electrode upon sequential coating of MWNTs and $V_2O_5$ NWs (CMV)
Figure 1D:
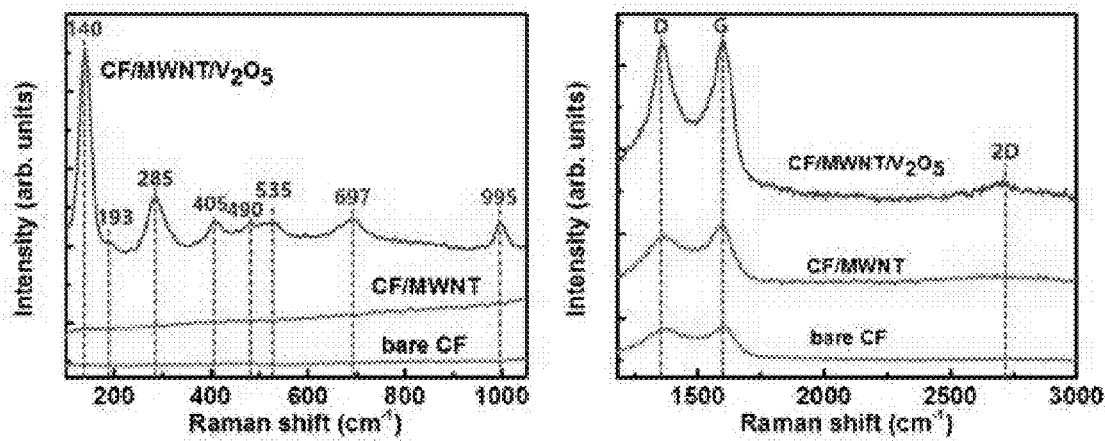
FIG. 1d shows Raman spectra of CF, CM, and CMV electrodes.
Figure 1E:
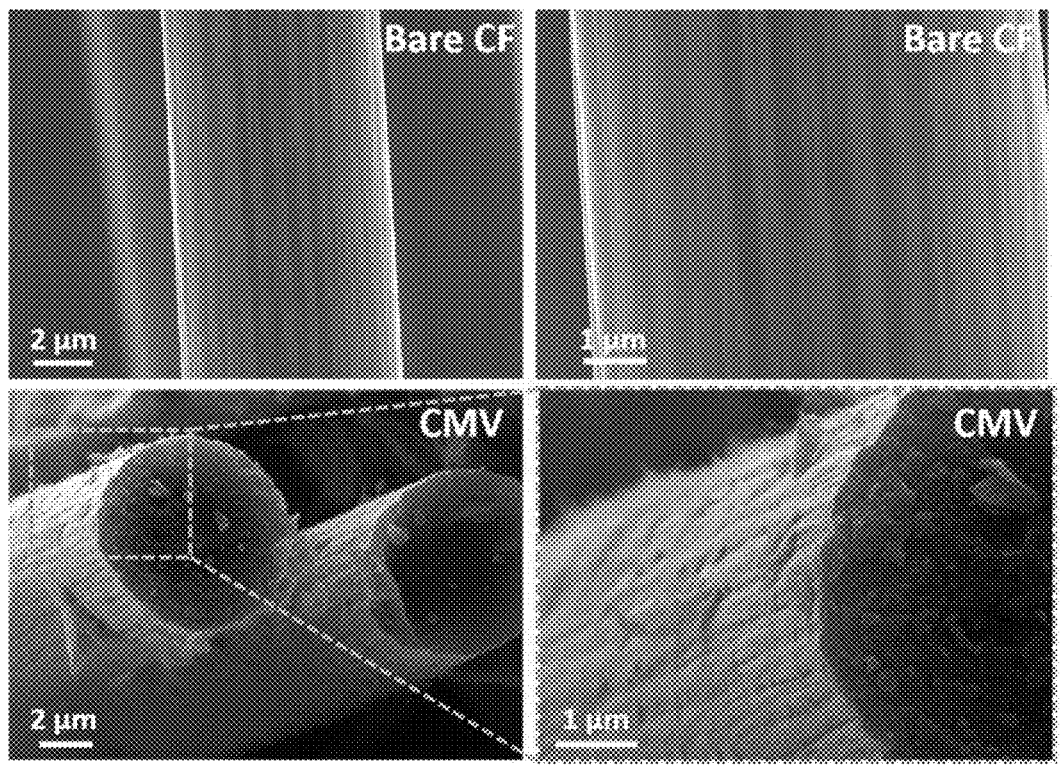
FIG. 1e shows additional SEM images of carbon fiber and cross-sectional SEM images of the CMV electrode.

FIG. 1c represents SEM images of the bare carbon fiber (CF) electrode, CF electrode coated with MWNTs (CM), CF electrode coated with $V_2O_5$ NWs (CV), and CF electrode upon sequential coating of MWNTs and $V_2O_5$ NWs (CMV). Pristine CF originally had a smooth surface while after coating of MWNTs and then $V_2O_5$ NWs, exhibited a rough surface morphology, showing nanowires adsorbed on its surface. FIG. 1d shows Raman spectra of bare CF, CM, and CMV electrode. Raman spectra confirmed the existence of $V_2O_5$ NWs: All samples had carbon fiber electrode in common, thus exhibited carbon peaks between 1200 and 3000 $cm^{-1}$. However, $V_2O_5$ peaks between 100 and 1100 cm' were only shown in CMV electrode. Additional SEM images of the bare carbon fiber (CF) and cross-sectional SEM images of the CMV electrode are shown in FIG. 1e.

Figure 1F:
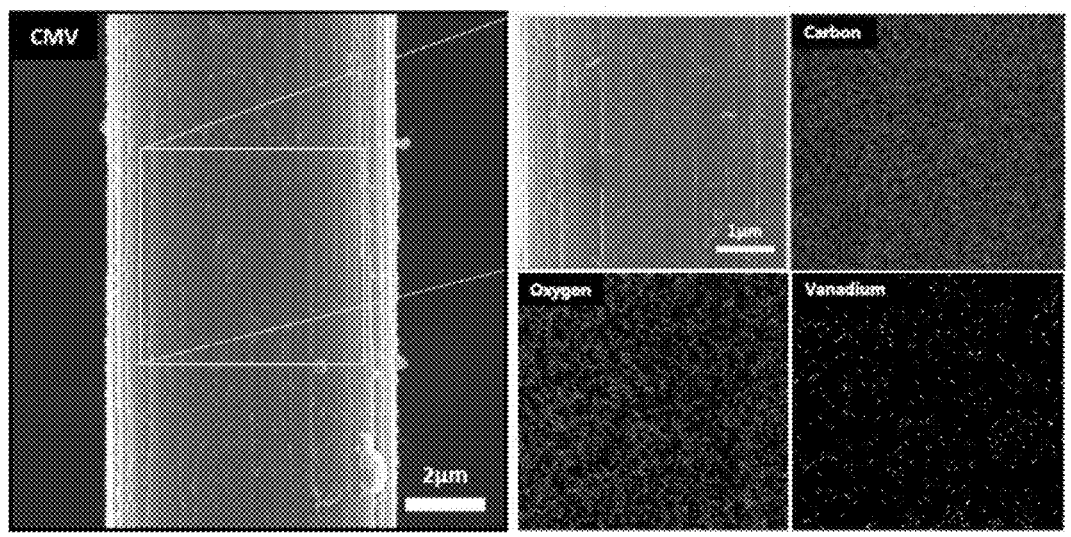
FIG. 1f shows surface images of the CMV electrode via EDS mapping.

FIG. 1f shows surface images of the CMV electrode via EDS mapping. Pristine carbon fiber had a smooth surface and CMVs comprised MWNTs and $V_2O_5$ NWs on the carbon fiber surface. Furthermore, the existence of $V_2O_5$ NWs coated on the CMV surface was confirmed via EDX mapping. The MWNTs were attached onto the carbon fiber surface via van der Waals interaction, and $V_2O_5$ NWs were then attached onto the CF/MWNT surface through attractions between polar surfaces. A similar profile was reported also in previous studies. NWs are not attracted by negatively charged surface regions but are aligned on polar surface regions compared to on nonpolar regions (S. Myung, M. Lee, G. T. Kim, J. S. Ha and S. Hong, Adv. Mater., 2005, 17, 2361).

Figures 3A, 3B, 3C, 3D:
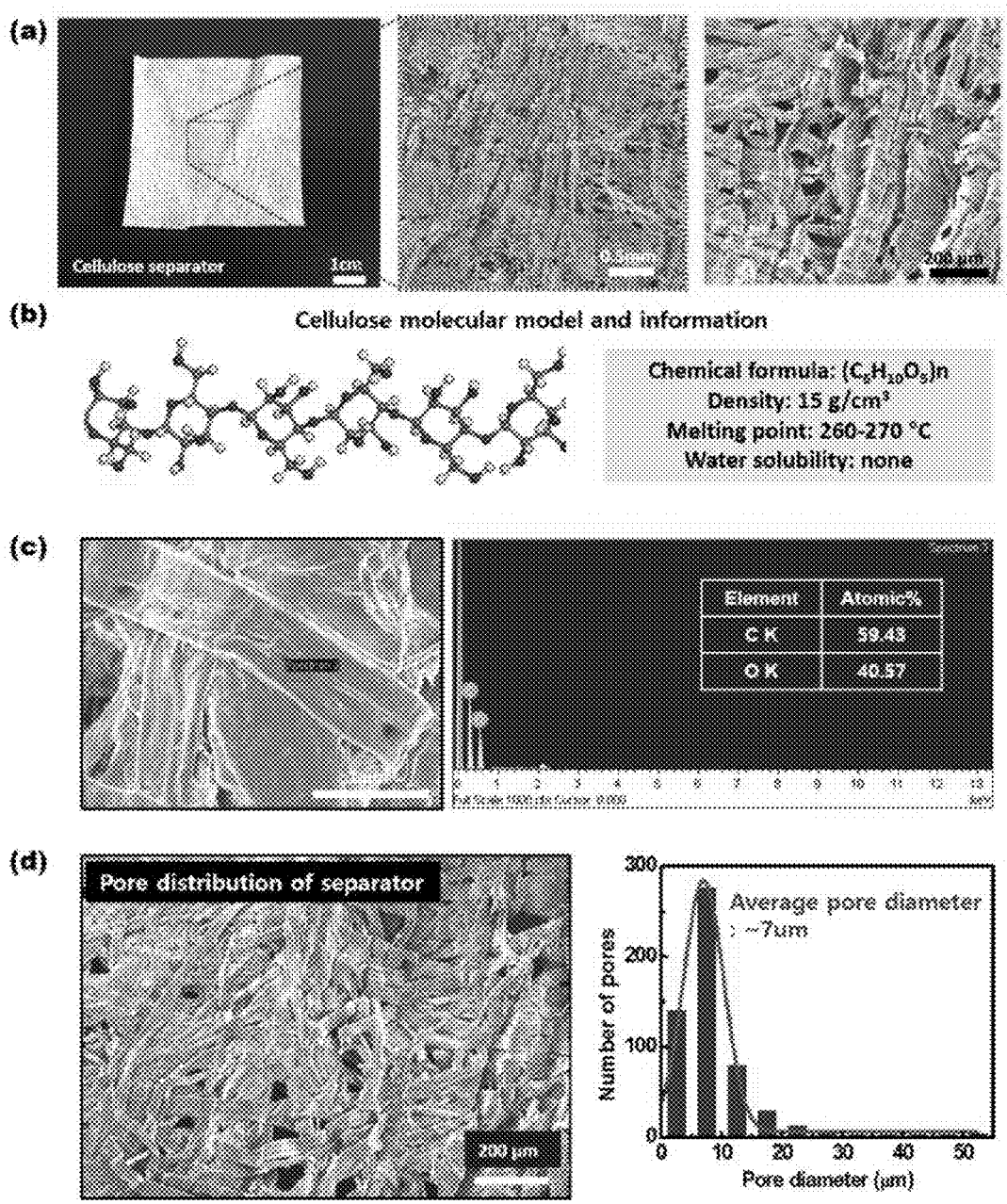
FIGS. 3a, 3b, 3c and 3d show (a) optical (left) and SEM images (middle and right) of a cellulose separator used in a wire-type supercapacitor according to the present invention, (b) a molecular model of the separator and information on the physical properties of the separator, (c) an optical image (left) and the results of elemental analysis (right) of the separator, and an EDX spectrum of the separator.

(a) of FIG. 3 shows optical (left) and SEM images (middle and right) the cellulose separator used in the wire-type supercapacitor of the present invention. The cellulose separator has a large number of pores with various sizes, which can also be seen from the magnified SEM images, and is composed only of carbon, hydrogen and oxygen ($C_6H_{10}O_5$), as confirmed by EDX analysis. The average pore diameter of the separator was estimated to be 7 μm based on image analysis ((b) to (d) of FIG. 3). Furthermore, the separator showed good wettability on the electrolyte and provided effective insulation between the two electrodes. In previous studies, solid-state electrolytes based on PVA and acid have been used in similar systems (X. Pu, L. Li, M. Liu, C. Jiang, C. Du, Z. Zhao, W. Hu and Z. L. Wang, Adv. Mater., 2016, 28, 98, etc,), but such electrolytes have limitations in applying to high performance wire supercapacitors due to their low operation voltage and solvent (water) evaporation in ambient conditions (D. Kim, G. Lee, D. Kim and J. S. Ha, ACS Appl. Mater. Interfaces, 2015, 7, 4608). To overcome these drawbacks, the present inventors synthesized a Li ion-assisted, ionic liquid based solid-state electrolyte with an extended voltage window of 1.5 V.

Figures 4A, 4B, 4C, 4D:
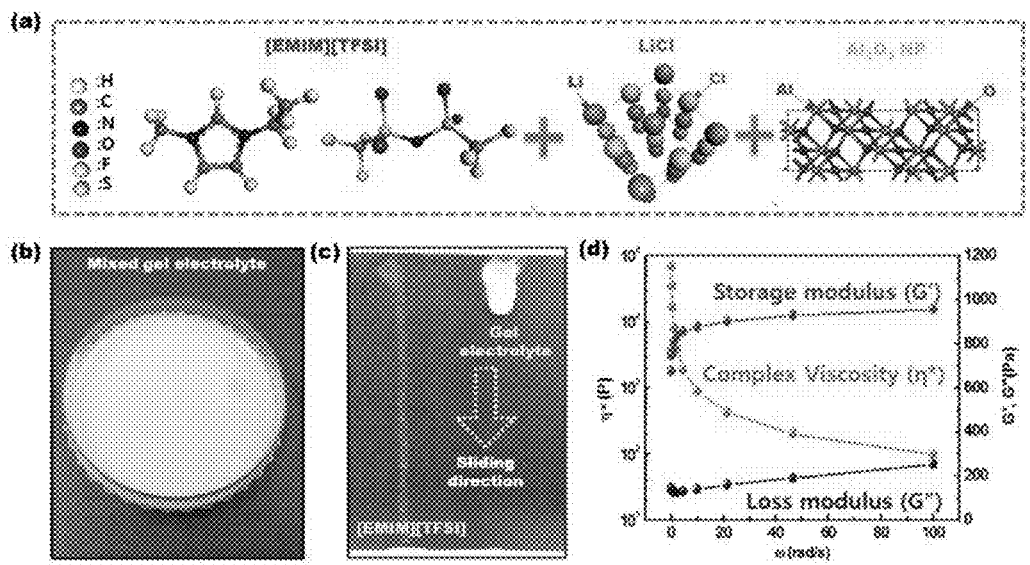
FIGS. 4a, 4b, 4c and 4d show (a) molecular models of electrolyte components used in a wire-type supercapacitor of the present invention, (b) an image of a mixed solid-state electrolyte, (c) measured viscosity of the electrolyte, and (d) rheological properties of the electrolyte.

(a) of FIG. 4 shows molecular models of the electrolyte components. The solid-state electrolyte consists of [EMIM] [TFSI], LiCl, and $Al_2O_3$ NPs. [EMIM][TFSI] has a high voltage window of 1.5 V, and LiCl provides Li ion to the $V_2O_5$ NWs which increases the capacitance of the wire supercapacitor. $Al_2O_3$ NPs play an important role in controlling the viscosity of the solid-state electrolyte. (b) of FIG. 4 shows an image of the mixed solid-state electrolyte. The electrolyte was colored white due to $Al_2O_3$NPs and had a higher viscosity than the ionic liquid ((c) of FIG. 4). The viscosity of the ionic liquid was 61.14 cP at 25 □ whereas the complex viscosity of the electrolyte was ~$10^5$ poise (1 poise=100 cP=0.1 Pa·s) in the low angular frequency range at 25 □. Furthermore, the measured storage modulus was 5 times higher than the loss modulus over the entire angular frequency range ((d) of FIG. 4). Such rheological analyses confirm the solid-like dynamics of the synthesized electrolyte.

Figures 5A, 5B, 5C, 5D, 5E:
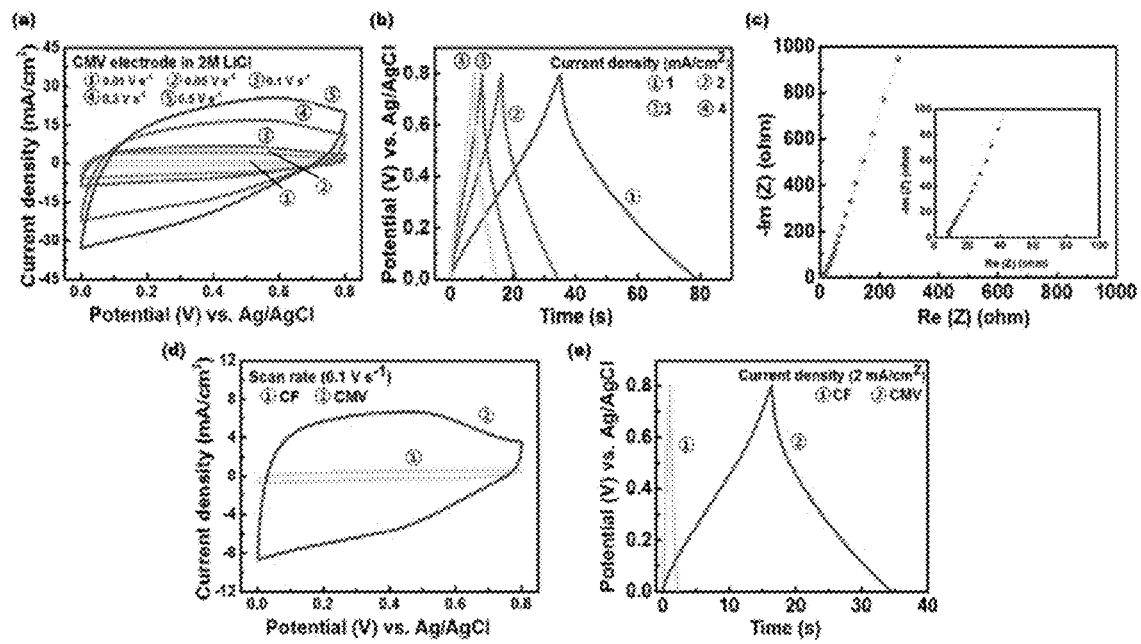
FIGS. 5a, 5b, 5c, 5d and 5e show (a) cyclic voltammetry (CV) curves of a CMV electrode at various scan rates, (b) charge-discharge curves of the CMV electrode at various current densities, (c) a Nyquist plot of the CMV electrode, (d) performance of the carbon fiber and the CMV electrode at various scan rates, and (e) charge-discharge curves of the carbon fiber and the CMV electrode at the same current density.

FIG. 5 shows the results of 3-electrode electrochemical analysis for the carbon fiber electrode and the CMW electrode in 2 M LiCl solution. Here, Pt wire and Ag/AgCl were used as the counter and reference electrodes, respectively. Specifically, FIG. 5 shows (a) CV curves of the CMV electrode at various scan rates, (b) charge-discharge curves of the CMV electrode at various current densities, (c) a Nyquist plot of the CMV electrode, (d) performance of the carbon fiber and the CMV electrode at various scan rates, and (e) charge-discharge curves of the carbon fiber and the CMV electrode at the same current density.

Pseudocapacitive behavior of a material is generally confirmed by 3-electrode electrochemical analysis which exhibits 1) rectangular shape in cyclic voltammetry, 2) symmetrical triangular shape in galvanostatic charge-discharge indicating an ideal capacitive behavior, and 3) a vertical line in Nyquist plot with phase angle equal to or lower than 90° in AC impedance test. Here, the pseudocapacitance of $V_2O_5$ was confirmed in 3-electrode electrochemical analysis including cyclic voltammetry, galvanostatic charge-discharge, and Nyquist plot as shown in FIG. 5.

Figures 6A, 6B, 6C, 6D, 6E, 6F:
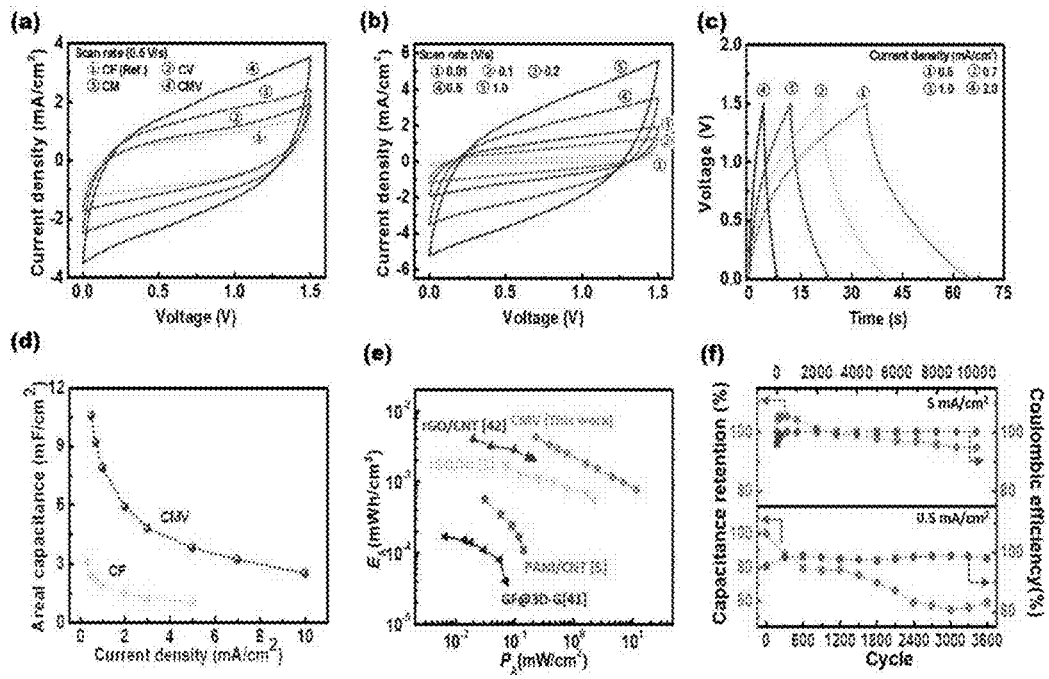
FIGS. 6a, 6b, 6c, 6d, 6e and 6f show (a) CV curves of CF, $CF/V_2O_5$, NWs (CV), F/MWNTs (CM), and CMV electrodes at a scan rate of 0.5 V/s, (b) CV curves of a wire-type supercapacitor with CMV electrodes at various scan rates, (c) charge-discharge curves obtained at various current densities, (d) areal capacitances of CF and CMV based wire-type supercapacitors with various current densities, (e) Ragone plot, and (f) capacitance retention and coulombic efficiency as a function of cycle.

CV curves of CF, CF/$V_2O_5$ NW (CV), CF/MWNT (CM) and CMV electrodes were obtained at a scan rate of 0.5 V/s as shown in (a) of FIG. 6. CMV showed the highest capacitance compared to other wire-type supercapacitors, presumably for the following reasons. When $V_2O_5$ and NWs were coated on the CF surface, the capacitance did not significantly increase, which is thought to be because NWs were not uniformly adsorbed on the CF surface. When MWNTs were coated on the CF surface, the capacitance increased slightly owing to the increased surface area and higher conductivity. However, the wire-type supercapacitor with CM electrodes did not exhibit pseudocapacitance induced from $V_2O_5$ NWs. Thus, it can be concluded that the wire-type supercapacitor with CMV electrodes is an ideal candidate material as a high-performance wire-type supercapacitor because it possesses a synergistic effect of CV and CM. Here, the insertion of $Li^+$ into $V_2O_5$ NWs can be represented by $V_2O_5 + xLi^+ + xe^- \leftrightarrow Li_xV_2O_5$, where x is a mole fraction of $Li^+$ ion.

(b) of FIG. 6 presents CV curves of the wire-type supercapacitor with CMV electrodes at various scan rates. The rectangular shape curves reflect ideal performance of the fabricated wire-type supercapacitor. (c) of FIG. 6 shows charge/discharge curves obtained at various current densities. The areal capacitance of the wire-type supercapacitor estimated from the charge/discharge curves was 10.6 mF/$cm^2$ at a current density of 0.5 mA/$cm^2$, but decreased at increased current densities as shown in (d) of FIG. 6. The areal capacitance of the wire-type supercapacitor with CMV electrode was 5 times higher than that of CF.

Figures 7A, 7B, 7C:
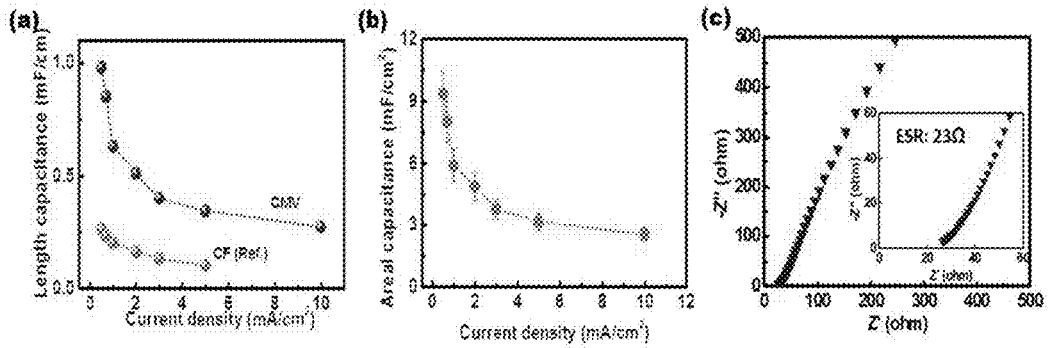
FIGS. 7a, 7b and 7c show (a) length capacitances of CF and CMV electrodes at various current densities, (b) areal capacitances of the CF and CMV electrodes, and (c) a Nyquist plot.

(a) of FIG. 7 indicates a length capacitance of 0.98 mF/cm at a current density of 0.5 mA/$cm^2$. The capacitance of the wire-type supercapacitor ($C_{cell}$) and areal or length capacitances in a two-electrode cell were calculated from their charge/discharge curves at different current densities using the following equations:

$$C_{cell} = \frac{I \cdot \Delta t}{\Delta V} \quad (1)$$

$$C_M = \frac{C_{cell}}{M} \quad (2)$$

where I, $\Delta V$, $\Delta t$ and M correspond to discharge current, voltage range (excluding IR-drop), discharge time and length or area of the wire-type supercapacitor, respectively. Furthermore, the average areal capacitance estimated from five wire-type supercapacitor samples was quite uniform, showing a standard deviation value smaller than 10% ((b) of FIG. 7).

The specific capacitance values correspond to capacitances at a very high level reported recently. Table 1 compares $C_{sp}$ values of the inventive wire-type supercapacitor to other recently reported $C_{sp}$ values.

TABLE 1

| Electrode materials | $C_A$ (mF/cm$^2$) | $C_L$ (mF/cm) | characterization conditions |
|---|---|---|---|
| CF/MWNT/V$_2$O$_5$ NW (this work) | 2.5-10.6 | 0.27-2.39 | GCD$^{(a)}$: 0.5-10.0 mA/cm$^2$ |
| rGo-Ni-yarn [1] | 27.7-49.4 | 5.0-8.9 | GCD: 1.0-10.0 mA/cm$^2$ |
| MnO$_2$/CNT fiber [2] | 13.9-15.9 | 0.13-0.15 | GCD: 0.6-5.7 mA/cm$^2$ |
| graphene/graphene fiber [3] | 1.2-1.7 | 0.020 | GCD: 17-424.6 μA/cm$^2$ |
| TiO$_2$ nanotubes on wire and CNT fiber [4] | 0.6 | 0.024 | GCD: 0.25 μA |
| MWNT/MnO$_2$ composite fiber [5] | 3.2-3.6 | 0.016-0.019 | GCD: 0.5-10 μA |
| CNT fiber springs [6] | 27.07 | 0.51 | GCD: 150 mA/cm$^3$ |
| CNT fiber, CNT film [7] | 8.66 | 0.029 | GCD: 1.0 μA |
| CNT fiber [8] | 4.6 | — | CV$^{(b)}$: 50 mV/s |
| Pen ink/carbon fiber [9] | 11.9-19.5 | 0.504 | GCD: 0.083-16.7 mA/cm$^2$ |

* "this work": Inventive
[1] X. Pu, L. Li, M. Liu, C. Jiang, C. Du, Z. Zhao, W. Hu, Z. L. Wang, Advanced Materials, 28 (2016) 98-105.
[2] P. Xu, B. Wei, Z. Cao, J. Zheng, K. Gong, F. Li, J. Yu, Q. Li, W. Lu, J.-H. Byun, B.-S. Kim, Y. Yan, T.-W. Chou, ACS Nano, 9 (2015) 6088-6096.
[3] Y. Meng, Y. Zhao, C. Hu, H. Cheng, Y. Hu, Z. Zhang, G. Shi, L. Qu, Advanced Materials, 25 (2013) 2326-2331.
[4] T. Chen, L. Qiu, Z. Yang, Z. Cai, J. Ren, H. Li, H. Lin, X. Sun, H. Peng, Angewandte Chemie International Edition, 51 (2012) 11977-11980.
[5] J. Ren, L. Li, C. Chen, X. Chen, Z. Cai, L. Qiu, Y. Wang, X. Zhu, H. Peng, Advanced Materials, 25 (2013) 1155-1159.
[6] Y. Zhang, W. Bai, X. Cheng, J. Ren, W. Weng, P. Chen, X. Fang, Z. Zhang, H. Peng, Angewandte Chemie International Edition, 53 (2014) 14564-14568.
[7] X. Chen, L. Qiu, J. Ren, G. Guan, H. Lin, Z. Zhang, P. Chen, Y. Wang, H. Peng, Advanced Materials, 25 (2013) 6436-6441.
[8] P. Xu, T. Gu, Z. Cao, B. Wei, J. Yu, F. Li, J.-H. Byun, W. Lu, Q. Li, T.-W. Chou, Advanced Energy Materials, 4 (2014) 1300759-n/a.
[9] Y. Fu, X. Cai, H. Wu, Z. Lv, S. Hou, M. Peng, X. Yu, D. Zou, Advanced Materials, 24 (2012) 5713-5718.

The equivalent serial resistance (ESR) of the wire-type supercapacitor was measured to be 23Ω from the Nyquist plot shown in (c) of FIG. 7. Energy density (EA) and power density ($P_A$) values were calculated using the following equations:

$$E_A = \frac{C_A \cdot \Delta V^2}{7200} \quad (4)$$

$$P_A = \frac{E_A \cdot 3600}{\Delta t} \quad (5)$$

In Ragone plot shown in (e) of FIG. 6, energy and power densities of the inventive wire-type supercapacitor were compared with those from other groups, calculated in the same manner. The inventive WSC with CMV electrodes had an energy density of 3.31 μWh/cm$^2$ at a power density of 0.378 mW/cm$^2$ and a power density of 11.7 mW/cm$^2$ at an energy density of 0.78 μWh/cm$^2$, which is relatively high compared to those of wire-type supercapacitors with rGO fiber (0.17 μWh/cm$^2$, 0.02 mW/cm$^2$) (Y. Huang, H. Hu, Y. Huang, M. Zhu, W. Meng, C. Liu, Z. Pei, C. Hao, Z. Wang and C. Zhi, ACS Nano, 2015, 9, 4766), rGO/CNT (3.84 μWh/cm$^2$, 0.02 mW/cm$^2$) (L. Kou, T. Huang, B. Zheng, Y. Han, X. Zhao, K. Gopalsamy, H. Sun and C. Gao, Nat. Commun., 2014, 5, 374), and rGO/Ni (0.6 μWh/cm$^2$, 2.42 mW/cm$^2$) (X. Pu, L. Li, M. Liu, C. Jiang, C. Du, Z. Zhao, W. Hu and Z. L. Wang, Adv. Mater., 2016, 28, 98) electrodes, indicating the superior performance of the inventive WSC.

It is also important to achieve long cycling durability in addition to good electrochemical performance. (f) of FIG. 6 shows stable cycling stability of the fabricated wire-type supercapacitors at a high current density of 5 mA/cm$^2$; ~94.6% of the initial capacitance was retained and 100% of the columbic efficiency was maintained after 10,000 cycles. Furthermore, the triangular shapes of the charge/discharge curves almost remained unchanged even after 10,000 cycles (see the inset of (f) of FIG. 6).

However, there is a limitation to show device stability of the supercapacitor at a high current density. To evaluate device stability, cyclic evaluation was conducted at a low current density of 0.5 mA/cm$^2$ for prolonged period of time. After 3600 galvanostatic charge-discharge cycle at 0.5 mA/cm$^2$ for 40 h, the capacitance of the supercapacitor retained 58.8% of its original value and showed average coulombic efficiency of 98%. The reason for low cyclic stability of the supercapacitor is not clear, but it may be caused by pseudocapacitance of V$_2$O$_5$; the reaction between the electrode and electrolyte may have reduced surface area and/or increased resistance in V$_2$O$_5$ for charge transportation during cycling process.

Figures 8A, 8B, 8C, 8D, 8E, 8F:
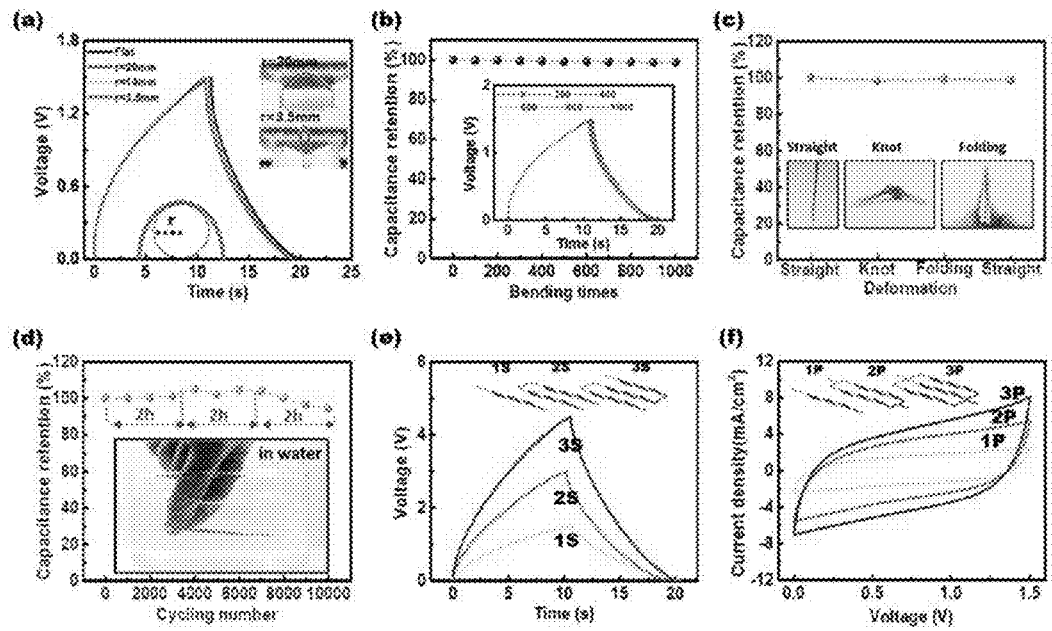
FIGS. 8a, 8b, 8c, 8d, 8e and 8f show (a) mechanical stability of a wire-type supercapacitor according to the present invention at different bending radii, (b) changes in capacitance retention as a function of bending times, (c) changes in capacitance retention under mechanical deformations, (d) changes in the capacitance retention of the wire-type supercapacitor as a function of cycling number in water, (e) changes in the voltage of two and three wire-type supercapacitors connected in series as a function of time, and (f) changes in the current of two and three wire-type supercapacitors connected in parallel as a function of time.

(a) of FIG. 8 shows the mechanical stability of the inventive wire-type supercapacitor under bending at different bending radii. Stable operation of the inventive wire-type supercapacitor was observed under bending at a radius (r) down to 3.5 mm. The inventive wire-type supercapacitor also retained 98.7% of its initial capacitance after 1000 bending cycles from flat to r=3.5 mm as shown in (b) of FIG. 8. The charge/discharge curves in the inset of (b) of FIG. 8 also show ideal triangular shapes, regardless of the number of bending cycles. The inventive wire-type supercapacitor also shows no noticeable deterioration under bent, knotted and folded states as shown in (c) of FIG. 8. The inset of (c) of FIG. 8 presents photographic images of straight, knotted and folded states, which confirm that the inventive wire-type supercapacitor is suitable for use in wearable devices.

Figures 9A, 9B:
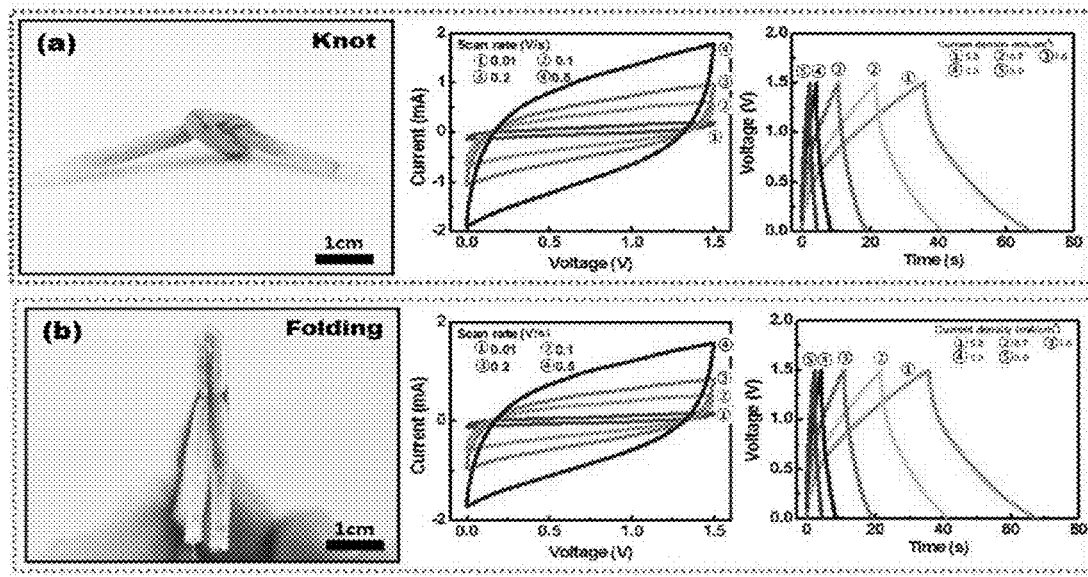
FIGS. 9a and 9b show photographic images, CV and charge-discharge curves of knotted and folded wire-type supercapacitors.

FIG. 9 shows photographic images, CV and charge/discharge curves of knotted and folded wire-type supercapacitors. Referring to FIG. 9, the two graphs show superior electrochemical properties even under deformation. Next, charge/discharge curves were measured at a scan rate of 5 mA/cm$^2$ while the wire-type supercapacitor was immersed in water. After more than 10,000 cycles of GCD for 6 h, almost 100% of the initial capacitance was retained ((d) of FIG. 8). The stable performance of the serially and parallel connected wire-type supercapacitors was also confirmed; when two and three wire-type supercapacitors were connected serially, the operation voltages increased to 3.0 V and 4.5 V, respectively, and the operation time remained the same ((e) of FIG. 8). When two and three wire-type supercapacitors were connected in parallel, each cell capacitance increased by about two (2.04 mF) and three (2.87 mF) times at a scan rate of 0.5 V/s, respectively ((f) of FIG. 8). The stable electrochemical performance of the serially and parallel connected wire-type supercapacitors confirms the fact that the inventive wire-type supercapacitor can be applied to various electronic circuits of wearable devices.

Figures 10A, 10B, 10C, 10D:
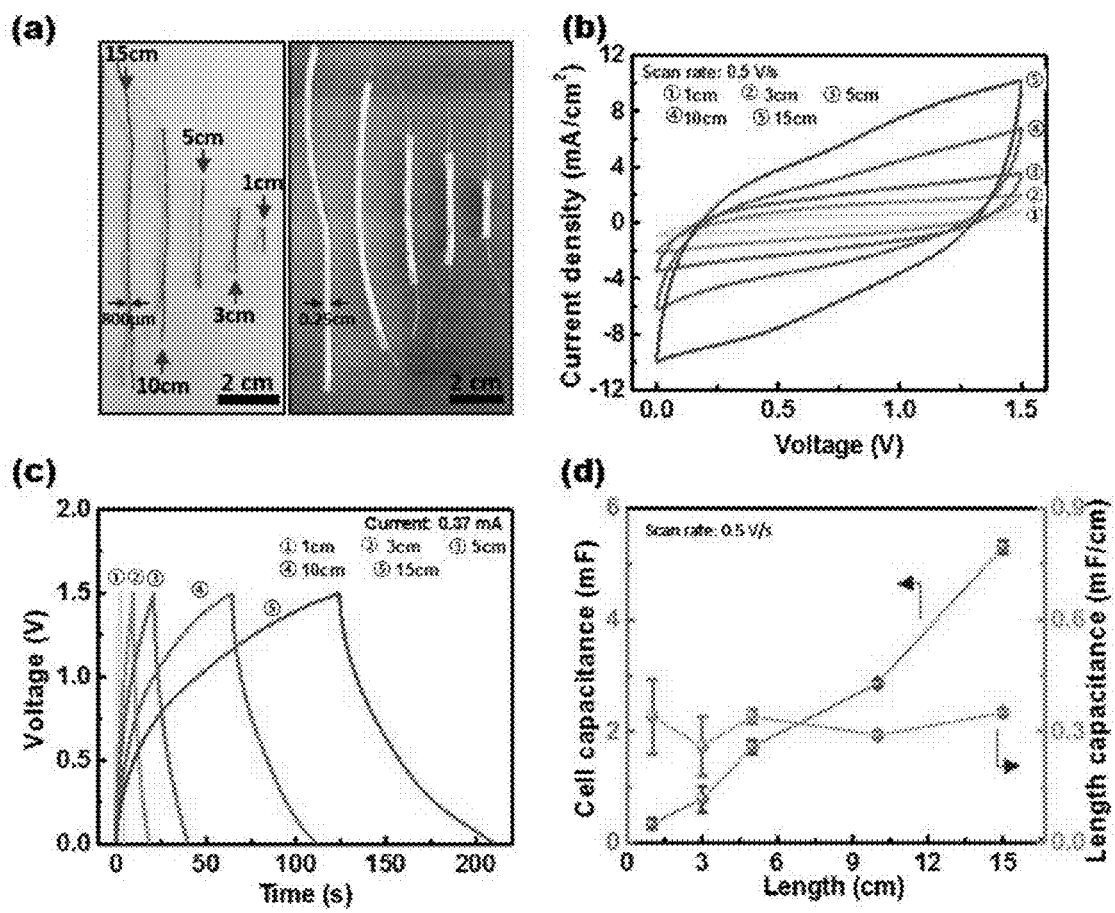
FIGS. 10a, 10b, 10c and 10d show (a) optical images of CMV electrodes (left) and wire-type capacitors (right) with varying lengths of 1-15 cm, (b) and (c) charge-discharge current and discharge time, respectively, and (d) cell and length capacitance of wire-type supercapacitors as a function of wire-type supercapacitor length.

(a) of FIG. 10 shows photographic images of the CMV electrode (left) and wire-type supercapacitor (right) with varying lengths of 1-15 cm. With increasing the length of the wire-type supercapacitor, the capacitance and the discharge time increased ((b) and (c) of FIG. 10). (d) of FIG. 10 shows cell and length capacitance as a function of wire-type supercapacitor length. Cell capacitance increased linearly with the wire-type supercapacitor length whereas the length capacitance of ~0.3 mF/cm was retained regardless of the total wire-type supercapacitor length. Moreover, the average capacitance estimated from three different wire-type supercapacitors was quite uniform except for the very short wire-type supercapacitors (<3 cm) due to their large distribution of resistance values. Such a uniform length capacitance over varying lengths is attributed to the markedly increased capacitance compared to the increased resistance with the increase in length. This result implies the high potential of the inventive wire-type supercapacitor for use in energy storage devices, which require long wire-type supercapacitors with high capacitance but with minimal loss of capacitance.

The fabricated wire-type supercapacitors can operate wire-type environmental sensors integrated on a fabric. A $NO_2$ gas sensor was fabricated by coating MWNTs on a wool wire. As shown in (a) of FIG. 11, the wire-shaped $NO_2$ gas sensor and the fabricated wire-type supercapacitors were integrated on a fabric via knitting. With three wire-type supercapacitors connected in parallel, the sensor could stably operate for 400 s. The on/off current ratio with exposure to $NO_2$ gas was almost the same as that observed when using a 1 V battery. Adsorption of $NO_2$ gas onto air-exposed p-MWNT extracts electrons from electron-hole (e-h) pairs to form adsorbed $NO_2$" on the MWNT surface. As a result, the hole concentration of the MWNT increases, increasing the current.

Next, two wire-type UV sensors to detect 365 nm UV light with spiropyran (SP) and ZnO NWs grown on PU wires were fabricated. Upon exposure to UV, SP coated PU wire changed its color and a photocurrent from ZnO NWs could be detected with three wire-type supercapacitors in parallel ((b) of FIG. 11). The transparent SP sensor changed into purple color under UV light: SP molecule consists of two heterocyclic functional groups in orthogonal planes bound by a carbon atom. SP does not show photochromic properties in the solid state but may change its color in the solution or dry state upon exposure to UV with a wavelength of 250-380 nm. By breaking the C—O bonds, UV light transforms SP into the color-emitting merocyanine (MC) form. The structure of the colorless molecules is more thermodynamically stable than the product, which indicates their dependence on storage solvents. Molecular models of the photoreaction between SP and MC are shown in (a) of FIG. 12.

(b) of FIG. 12 shows SEM images taken from PU wires before (top) and after (bottom) the growth of ZnO NWs. The average length and diameter of the ZnO NWs were 7.5 μm and 1.0 μm, respectively. The ZnO NW sensor was operated for 700 s using charged WSCs under exposure to 365 nm UV light at an intensity of 0.7 mW/cm². A constant photocurrent of 120 nA was measured during UV detection. The sensitivity of the ZnO NW sensor was approximately 4, based on the following equation:

$$\text{Photosensitivity} = \frac{I_{light} - I_{dark}}{I_{dark}} = \frac{I_{ph}}{I_{dark}} \qquad (6)$$

where $I_{light}$, $I_{dark}$, and $I_{ph}$ are the current with UV light, current without UV light, and the photocurrent, respectively. The sensitivity of the sensor was not high compared to the values in previously reported studies but the inventive wire-type sensor has more suitable characteristics for use in wearable systems.

Figures 11A, 11B, 11C, 11D:
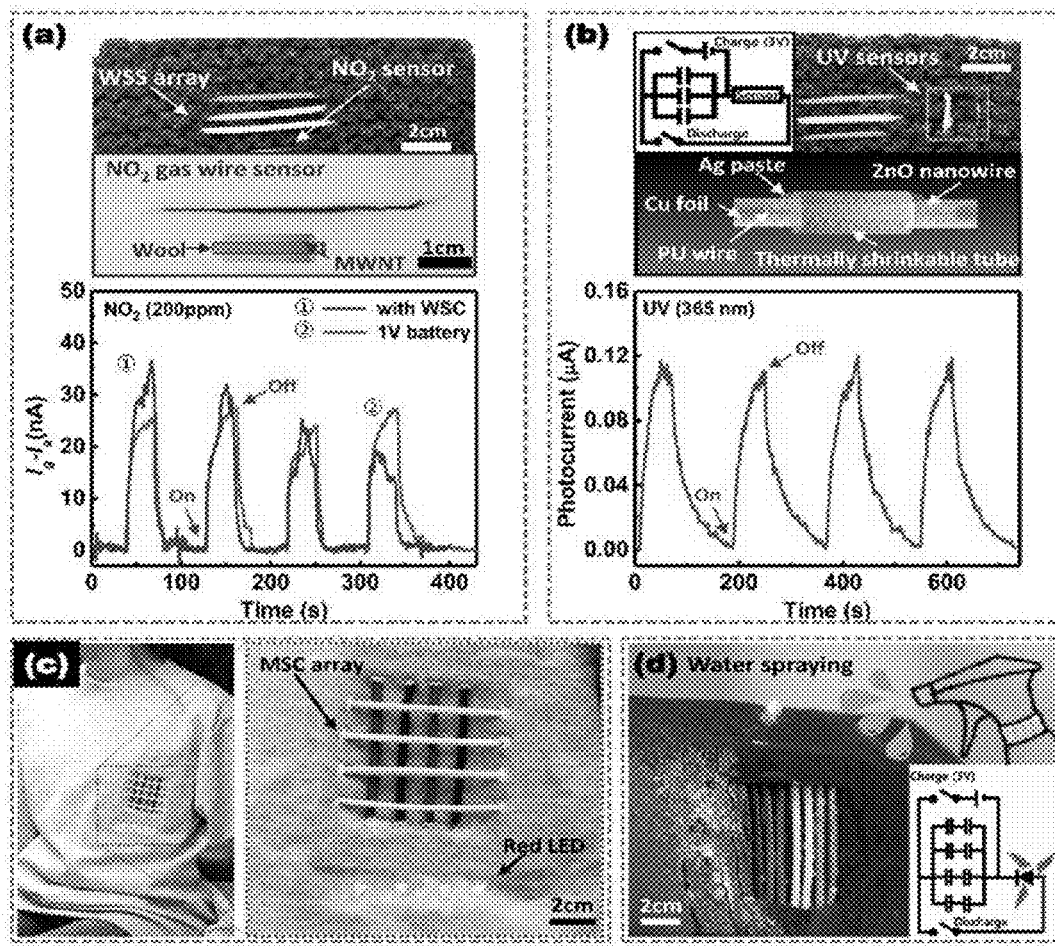
FIGS. 11a, 11b, 11c and 11d show (a) an optical image of an integrated wire shaped $NO_2$ gas sensor and wire-type supercapacitor array on fabric and operating characteristics of the array as a function of time, (b) an optical image of an integrated wire shaped UV sensor and WSC array on fabric and operating characteristics of the array as a function of time, and (c) and (d) photographs of an array of two serial and four parallel connected (2S4P) wire-type supercapacitors knitted on a on cloth and a water-proof fabric, respectively.

Next, an array of two serial and four parallel connected (2S4P) wire-type supercapacitors was knitted on a cloth and on a water-proof fabric ((c) and (d) of FIG. 11). The operating voltage and capacitance of the 2S4P array were two times higher than those of a single wire-type supercapacitor.

Figure 13:
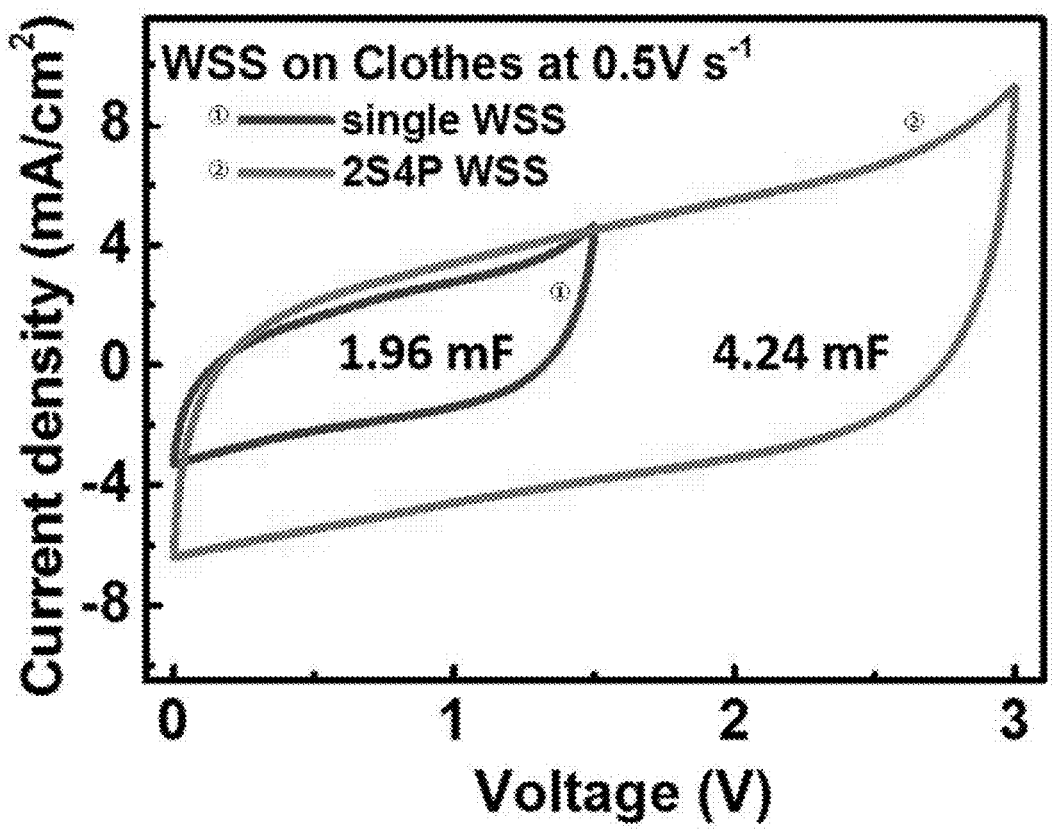
FIG. 13 shows CV curves of a 2S4P wire-type supercapacitor and a single wire-type supercapacitor.

FIG. 13 shows CV curves of the 2S4P wire-type supercapacitor and the single wire-type supercapacitor. The 2S4P WSC circuit is shown in the inset of (d) of FIG. 12. After being charged with a battery for 1 min, the wire-type supercapacitor array operated four LEDs as shown in (c) of FIG. 12. Furthermore, a WSC array knitted on a water-proof fabric stably operated LEDs under water spraying conditions ((d) of FIG. 11).

In summary, high performance wire-type supercapacitor arrays integrated with UV/$NO_2$ sensors on textiles were fabricated. With CMV electrodes, a cellulose separator, and an ionic liquid solid state electrolyte with Li salt, the fabricated wire-type supercapacitor exhibited excellent mechanical stability under deformation as well as good electrochemical performance, with extended voltage window of 1.5 V and an areal capacitance of 89.6 mF/cm². Furthermore, encapsulation guaranteed stable performance of the inventive wire-type supercapacitors under water, and the wire-type supercapacitor array successfully operated integrated wire-type $NO_2$ gas and UV sensors on a textile. The above results suggest a successful potential application of the inventive wire-type supercapacitors in various wearable devices.

What is claimed is:

1. A wire shaped carbon fiber electrode comprising:
   braided strings of carbon fiber coated with a plurality of sequentially formed carbon nanotube layers, the carbon nanotubes being coated with a plurality of sequentially formed nanowire layers;
   wherein a number of sequentially formed carbon nanotube layers is different than a number of sequentially formed nanowire layers.

2. The wire shaped carbon fiber electrode according to claim 1, wherein the wire shaped carbon fiber electrode comprises three strings of carbon fiber.

3. The wire shaped carbon fiber electrode according to claim 1, wherein the number of sequentially formed carbon nanotube layers is greater than the number of sequentially formed $V_2O_5$ nanowire layers.

4. The wire shaped carbon fiber electrode according to claim 3, wherein the sequentially formed nanowire layers comprise $V_2O_5$ nanowires.

5. A wire-type supercapacitor comprising:
   the wire shaped carbon fiber electrode;
   a solid-state electrolyte; and
   a separator;

wherein the wire shaped carbon fiber electrode comprises braided strings of carbon fiber coated with a plurality of sequentially formed carbon nanotube layers, the carbon nanotubes being coated with a plurality of sequentially formed nanowire layers, characterized in that a number of sequentially formed carbon nanotube layers is different than a number of sequentially formed nanowire layers.

6. The wire-type supercapacitor according to claim 5, wherein the solid-state electrolyte comprises 1-ethyl-3-methylimidazolium bis(trifluoromethylsulfonyl)imide, LiCl, and $Al_2O_3$ nanoparticles.

7. The wire-type supercapacitor according to claim 6, wherein the separator is a cellulose separator.

8. A $NO_2$ sensor comprising:
a wire-type supercapacitor;
wherein the wire-type supercapacitor comprises solid-state electrolyte; a separator, and an wire shaped carbon fiber electrode comprising braided strings of carbon fiber coated with a plurality of sequentially formed carbon nanotube layers, the carbon nanotubes being coated with a plurality of sequentially formed nanowire layers, characterized in that a number of sequentially formed carbon nanotube layers is different than a number of sequentially formed nanowire layers.

9. A UV sensor comprising:
a wire-type supercapacitor;
wherein the wire-type supercapacitor comprises solid-state electrolyte; a separator, and an wire shaped carbon fiber electrode comprising braided strings of carbon fiber coated with a plurality of sequentially formed carbon nanotube layers, the carbon nanotubes being coated with a plurality of sequentially formed nanowire layers, characterized in that a number of sequentially formed carbon nanotube layers is different than a number of sequentially formed nanowire layers.

* * * * *